United States Patent [19]

Large et al.

[11] 3,956,486
[45] May 11, 1976

[54] INSECTICIDAL PHTHALIMIDOTHIOPHOSPHATES ACTIVATED WITH CERTAIN PHOSPHOROTHIONATES

[75] Inventors: George B. Large, Orinda; Leland S. Pitt, San Jose, both of Calif.

[73] Assignee: Stauffer Chemical Company, Westport, Conn.

[22] Filed: Dec. 30, 1974

[21] Appl. No.: 537,143

[52] U.S. Cl.................................. 424/200; 424/211
[51] Int. Cl.².......................................... A01N 9/36
[58] Field of Search............................ 424/200, 220

[56] References Cited
UNITED STATES PATENTS

| | | | |
|---|---|---|---|
| 2,767,194 | 10/1956 | Fancher............................ | 424/200 |
| 3,038,924 | 6/1962 | Schoot et al....................... | 424/220 |
| 3,760,043 | 9/1973 | Kishino et al...................... | 424/220 |

*Primary Examiner*—V. D. Turner
*Attorney, Agent, or Firm*—Daniel C. Block

[57] ABSTRACT

A composition of matter is described herein which is useful as an activator for insecticides. The activator composition is defined by the formula:

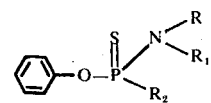

wherein R is selected from the group consisting of hydrogen and lower alkyl; $R_1$ is selected from the group consisting of hydrogen, alkyl and cycloalkyl; $R_2$ is selected from the group consisting of lower alkoxy and

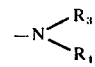

wherein $R_3$ and $R_4$ can be the same or different and are selected from the group consisting of hydrogen and lower alkyl.

26 Claims, No Drawings

INSECTICIDAL PHTHALIMIDOTHIOPHOSPHATES ACTIVATED WITH CERTAIN PHOSPHOROTHIONATES

BACKGROUND OF THE INVENTION

Among the many insecticidal compounds, the phthalimidothiophosphates have reached a relatively high degree of commercial success. These compounds are toxic to a large number of insect pests at different concentrations varying with the resistance of the insects mentioned. Some of these compounds are described in U.S. Pat. No. 2,767,194, specifically N-(mercaptomethyl) phthalimide-S-(O,O-dimethylphosphorodithioate).

The endeavor to extend the usefulness of the thiophosphates by increasing their effectiveness and lowering the cost has led to extensive studies on another class of biologically active chemicals, customarily referred to an synergists. Among the many synergists employed, the alkyl oxides, specifically, piperonyl butoxide, have been widely used. These compounds are described in U.S. Pat. Nos. 2,485,681 and 2,550,737.

DETAILED DESCRIPTION OF THE INVENTION

It has been discovered that the thiophosphate compounds having insecticidal activity can be increased by using an activator having the formula:

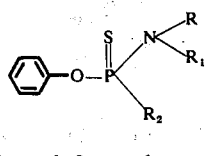

wherein R is selected from the group consisting of hydrogen and lower alkyl; $R_1$ is selected from the group consisting of hydrogen, alkyl and cycloalkyl; $R_2$ is selected from the group consisting of lower alkoxy and

wherein $R_3$ and $R_4$ can be the same or different and are selected from the group consisting of hydrogen and lower alkyl.

These compounds are manufactured by reacting an appropriate amine compound with certain halogenated phosphorothionate derivatives. After the end products are achieved, they are isolated and purified and admixed with the insecticidal compound. The amount of activator admixed therewith can range between 1 to 0.1 to about 1 to 10 parts insecticidal compound to activator compound. After the insecticidal compound and activator compound are mixed together, they are applied to the habitat of the insect in a conventional manner.

In order to illustrate the merits of the present invention, the following examples are provided:

EXAMPLE 1

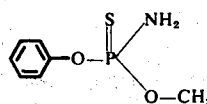

A solution was formed containing 5.8 grams (0.026 moles) of O-methyl-O-phenyl phosphorothiochloridate in 50 ml of benzene. Then, ammonia was bubbled into the stirring solution until no further reaction occurred. The resulting mixture was washed with $H_2O$, dried over anhydrous $MgSO_4$ then stripped under reduced pressure to yield 5.2 grams of product. $N_D^{30}$ 1.5396.

EXAMPLE 2

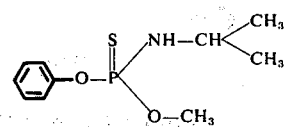

A solution was formed containing 5.6 grams (0.025 moles) of O-methyl-O-phenyl phosphorothiochloridate and 100 ml of benzene. To this solution was added 3.5 grams of isopropyl amine, portionwise. This mixture was stirred for ½ hour. The product was isolated by washing with dilute HCl solution followed by two $H_2O$ washes, dried over anhydrous $MgSO_4$ and the volitiles removed under reduced pressure to yield 5.5 grams of product. $N_D^{30}$ 1.5015.

EXAMPLE 3

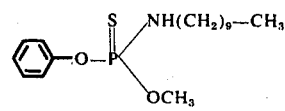

The procedure of Example 2 was repeated, except 9.4 grams of decyl amine was used. The yield was 8.6 grams. $N_D^{30}$ 1.4781.

EXAMPLE 4

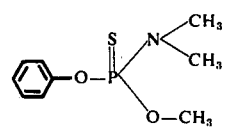

The procedure of Example 2 was repeated, except 2.7 grams of diethyl amine in a 40% aqueous solution was used. The yield was 5.8 grams of product. $N_D^{30}$ 1.5041.

EXAMPLE 5

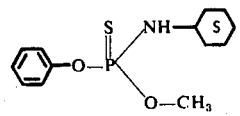

A solution was formed containing 5.6 grams (0.025 moles) of O-methyl-O-phenyl phosphorothiochloridate and 100 ml of benzene. To this solution was added 6.0 grams of cyclohexylamine, portionwise. The mixture was then refluxed for 45 minutes. The product was isolated in the same manner as in Example 2 to yield 7.1 grams of product. M.P. 43°–45°C.

EXAMPLE 6

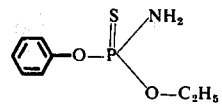

The procedure of Example 1 was repeated, except 5.9 grams (0.025 moles) of O-ethyl-O-phenyl phosphorothiochloridate was used. The yield was 5.4 grams of product. $N_D^{30}$ 1.5205.

EXAMPLE 7

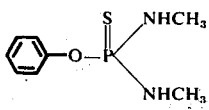

A solution was formed containing 5.7 grams (0.025 moles) of O-phenyl phosphorothiodichloridate and 100 ml of benzene. To this solution was added 3.26 grams of monomethylamine contained in a 40% aqueous solution. This mixture was stirred in a warm water bath for 15 minutes. The product was isolated in the same manner as in Example 2 to yield 5.0 grams of product. $N_D^{30}$ 1.5460.

EXAMPLE 8

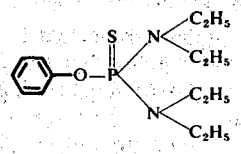

The procedure of Example 7 was repeated, except 7.6 grams of diethylamine was used. The yield was 6.0 grams. $N_D^{30}$ 1.5157.

Additional compounds were synthesized in a similar manner using appropriate starting materials. These compounds are listed in the following table.

TABLE I

| | | |
|---|---|---|
| Example 9 | Ph—O—P(=S)(NHCH₃)(OCH₃) | $N_D^{30}$ 1.5150 |
| Example 10 | Ph—O—P(=S)(NH—CH₂—CH(CH₃)₂)(OCH₃) | $N_D^{30}$ 1.4972 |
| Example 11 | Ph—O—P(=S)(N(C₂H₅)₂)(OCH₃) | $N_D^{30}$ 1.5071 |
| Example 12 | Ph—O—P(=S)(NH—(CH₂)₃—CH₃)(OCH₃) | $N_D^{30}$ 1.4976 |
| Example 13 | Ph—O—P(=S)(NH—CH(CH₃)—CH₂—CH₃)(OCH₃) | $N_D^{30}$ 1.4988 |
| Example 14 | Ph—O—P(=S)(NH—(CH₂)₅—CH₃)(OCH₃) | $N_D^{30}$ 1.4898 |
| Example 15 | Ph—O—P(=S)(NH(CH₂)₇—CH₃)(OCH₃) | $N_D^{30}$ 1.4822 |
| Example 16 | Ph—O—P(=S)(NH—(CH₂)₈—CH₃)(OCH₃) | $N_D^{30}$ 1.4805 |
| Example 17 | Ph—O—P(=S)(NH—CH₃)(OC₂H₅) | $N_D^{30}$ 1.5130 |
| Example 18 | Ph—O—P(=S)(NH—C₂H₅)(OC₂H₅) | $N_D^{30}$ 1.5058 |
| Example 19 | Ph—O—P(=S)(NH—CH₂—CH₂—CH₃)(OC₂H₅) | $N_D^{30}$ 1.5009 |
| Example 20 | Ph—O—P(=S)(NH(CH₂)₃—CH₃)(OC₂H₅) | $N_D^{30}$ 1.4927 |

TABLE I-continued

| | | |
|---|---|---|
| Example 21 | ⌬—O—P(=S)(NH(CH$_2$)$_4$—CH$_3$)(OC$_2$H$_5$) | $N_D^{30}$ 1.4888 |
| Example 22 | ⌬—O—P(=S)(NH$_2$)(O(CH$_2$)$_4$—CH$_3$) | $N_D^{30}$ 1.4955 |
| Example 23 | ⌬—O—P(=S)(NH—C$_2$H$_5$)(NH—C$_2$H$_5$) | $N_D^{30}$ 1.5267 |
| Example 24 | ⌬—O—P(=S)(NH—(CH$_2$)$_2$—CH$_3$)(NH—(CH$_2$)$_2$—CH$_3$) | $N_D^{30}$ 1.5136 |
| Example 25 | ⌬—O—P(=S)(NH—(CH$_2$)$_3$—CH$_3$)(NH—(CH$_2$)$_3$—CH$_3$) | M.P. 45–47°C |

INSECTICIDAL EVALUATION

A. House Fly [*Musca domestica* (L.)] (H.F.)

The following procedure was used to test both susceptible and S-chlorthion resistant houseflies. Test compounds are diluted in acetone and aliquots are pipetted onto the bottom of 55 × 15 mm aluminum dishes. To insure even spreading of the chemical on the bottom of the dishes, one ml of acetone containing 0.02% peanut oil is also added to each dish. After all solvents have evaporated the dishes are placed in circular cardboard cages containing 25 female houseflies. The cages are covered on the bottom with cellophane and the top with tulle netting, and each contains a sugar-water saturated cotton plug for maintenance of the flies. Mortality is recorded after 48 hours. Five parts activator are combined with one part toxicant in all stock solutions. Test levels range from 1,000 ug toxicant + 5,000 ug of activator down to that at which approximately 50% mortality occurs. All LD$_{50}$ values are expressed as ug of toxicant/dish.

B. Salt-marsh Caterpillar ]*Estigmene acrea* (Drury)] (SMC)

Test solutions are prepared by dissolving equal aliquots of the toxicant and activator in a 50—50 acetone-water solution. Sections of bitter dock (*Rumex obtusifolius*) leaves, 1–1.5 inches in length are immersed in the test solutions for 1–2 seconds and placed on a wire screen to dry. The dried leaf is placed on a moistened piece of filter paper in a Petri dish and infested with five third-instar larvae. Mortality of the larvae is recorded after 48 hours and the LD-50 values are expressed as percent toxicant in the acetone-water solutions.

C. Cabbage Looper [*Trichoplusia ni*] (CL)

Same as Salt-marsh Caterpillar (C), except that leaves of white cabbage (*Brassica oleracla*) are utilized as the host plant rather than bitter dock.

D. Tobacco Budworm [*Heliothis virescens* (F.)] (TBW)

Same as the Salt-marsh Caterpillar (C), except that leaves of Romaine lettuce (*Latuca sativa*) are utilized as the host plant rather than bitter dock.

E. German cockroach [*Blatella germanica* (Linne)] (GR)

Equal aliquots of toxicant and activator are diluted in a 50—50 acetone-water solution. Two cc of the solutions are sprayed through a DeVilbiss type EGA hand spray gun into circular cardboard cages containing ten one-month-old German cockroach nymphs. The test cages are covered on the bottom with cellophane and the top with tulle netting. Percent mortality is recorded 2 days later. Test concentrations range from 0.1% down to that at which approximately 50% mortality occurs. All LD$_{50}$ values are expressed as % toxicant.

F. Green Peach Aphid[*Myzus persicae* (Sulzer)] G.P.A.

Radish (*Raphanus sativus*) plants, approximately 1-2 inches tall, are transplanted into sandy loam soil in 3 inch clay pots and infested with 10–50 aphids of mixed ages. Twenty-four hours later they are sprayed, to the point of runoff, with a 50% water — 50% acetone solution containing the test compound or compounds. All combinations of technical materials are prepared with equal concentrations of toxicant and activator dissolved in the acetone/water solution. Test concentrations for both toxicant and activator ranged from .2% to that at which 50% mortality is obtained. Mortality is recorded after 48 hours and the LD$_{50}$ values are expressed as percent toxicant.

ACTIVATING FACTOR

The Activating Factor is arrived at by using the following formula from the expected response for a given combination of two insecticides.

$$A.F. = \frac{LD_{50} \text{ of Toxicant}}{\text{Experimental LD}_{50} \text{ of Combination}} \cdot \frac{1}{(xy+1)}$$

X = The ratio of the % or weight of the synergists to the % or weight of the toxicant.

Y = The ratio of the LD$_{50}$ of the toxicant to the LD$_{50}$ of the synergist.

The experimental LD$_{50}$ of the combination is in terms of the toxicant only.

The activating factor is therefore the ratio of the expected LD$_{50}$ of the combination divided by the experimental LD$_{50}$.

It is noted that when the observed response is greater than the expected, the Activating Factor is greater than one. This response is synergism. The results of these tests are set forth in Table II.

TABLE II

|  | Susceptable HF | Resistant HF | GR | SMC | CL | TBW | GPR |
|---|---|---|---|---|---|---|---|
| Insecticide* | 3.5 | >10,000 | 0.02 | >2.0 | 0.1 | 0.5 | .15 |
| Insecticide + Example 1 | 1.0 | <50.0 | 0.007 | >0.1 | >.03 | 0.02 | .02 |
| Example 1 | 30 | 500 | >0.1 | >0.1 | >.2 | 0.1 | .007 |
| Activating Factor | 2.2 | >2.0 | >2.38 | 1.0 |  | 4.17 | 2.52 |
| Insecticide + Example 2 | 1.5 | <50.0 | 0.01 | 0.1 | >.03 | 0.02 | .07 |
| Example 2 | 50 | 800 | >0.1 | >0.1 | .07 | 0.1 | .007 |
| Activating Factor | 1.73 | >3.15 | >1.67 | >1.0 |  | 4.17 | 6.82 |
| Insecticide + Example 3 | 2.8 | 75.0 | 0.02 | >0.1 | >.03 | 0.05 | .05 |
| Example 3 | >100 | 10,000 | >0.1 | >0.1 | >.2 | >0.1 | >.2 |
| Activating Factor | >1.0 | >22.22 | 1.0 | 1.0 | >1.17 | >1.7 |  |
| Insecticide + Example 4 | 2.8 | 90.0 | 0.02 | 0.07 | .02 | 0.02 | .02 |
| Example 4 | >100 | 10,000 | >0.1 | 0.1 | .1 | >0.1 | >.2 |
| Activating Factor | >1.0 | >18.52 | 1.0 | 1.3 | 2.5 | >4.2 | >4.3 |

|  | Susceptable HF | Resistant HF | GR | SMC | CL | TBW | Green Peach Aphid |
|---|---|---|---|---|---|---|---|
| Insecticide + Example 5 | 2.3 | 80.0 | 0.01 | >0.1 | >.1 | 0.05 | .02 |
| Example 5 | >100 | >10,000 | >0.1 | >0.1 | >0.2 | >0.1 | .18 |
| Activating Factor | >1.3 | >20.8 | >1.67 | 1.0 | 1.0 | >1.67 | 4.8 |
| Insecticide + Example 6 | 1.5 | 50.0 | 0.007 | 0.03 | 0.007 | 0.03 |  |
| Example 6 | 33 | 3,000 | >0.1 | >0.1 | >0.2 | >0.1 |  |
| Activating Factor | 1.5 | >11.3 | >2.4 | >3.2 | >9.5 | >2.8 |  |
| Insecticide + Example 7 | 2.8 | 50.0 | 0.02 | 0.05 | 0.02 | — | .03 |
| Example 7 | >100 | 3,000 | >0.1 | >0.1 | >.2 | >0.1 | >.2 |
| Activating Factor | >1.0 | >11.3 | 1.0 | — | >3.33 | — | >2.9 |
| Insecticide + Example 8 | 2.0 | 75.0 | 0.01 | 0.05 | 0.02 | 0.02 | .01 |
| Example 8 | >100 | 10,000 | >0.1 | 0.1 | 1 | >0.1 | .1 |
| Activating Factor | >1.5 | >22.22 | >1.67 | 1.9 | 2.5 | >4.2 | 6.0 |
| Insecticide + Example 9 | 2.0 | <50.0 | 0.007 | 0.05 | 0.02 | — | .01 |
| Example 9 | 88 | 3,000 | >0.1 | >0.1 | .15 | — | .15 |
| Activating Factor | 1.5 | >11.3 | >2.38 | >1.0 | 3.0 | — | 7.5 |
| Insecticide + Example 10 | 1.5 | 50.0 | 0.01 | 0.07 | 0.03 | 0.007 | .008 |
| Example 10 | >100 | 3,000 | >0.1 | 0.1 | .07 | >0.1 | .07 |
| Activating Factor | >2.0 | >11.3 | >1.67 | 1.0 | 1.4 | >11.9 | 5.96 |
| Insecticide + Example 11 | 2.0 | <50 | 0.01 | 0.05 | >0.03 | — | .02 |
| Example 11 | >100 | >10,000 | >0.1 | >0.1 | >.2 | — | .18 |
| Activating Factor | >1.49 | >33.3 | >1.67 | >1.9 | — | — | 4.1 |
| Insecticide + Example 12 | 1.8 | 50 | 0.02 | 0.1 | 0.03 | 0.05 | .02 |
| Example 12 | >100 | 800 | >0.1 | >0.1 | .05 | >0.1 | .2 |
| Activating Factor | >1.65 | >3.15 | 1.0 | >1.0 | 1.1 | >1.67 | 4.3 |
| Insecticide + Example 13 | 1.8 | <50.0 | 0.02 | 0.1 | 0.03 | 0.02 | .08 |
| Example 13 | 80 | 3,000 | >0.1 | >0.1 | .1 | >0.1 | .01 |
| Activating Factor | 1.6 | >11.32 | 1.0 | >1.0 | 1.67 | >4.17 | 5.2 |
| Insecticide + Example 14 | 2.0 | 80 | .02 | >0.1 | >0.03 | 0.08 | .02 |
| Example 14 | >100 | >10,000 | >0.1 | >0.1 | .15 | >0.1 | .18 |
| Activating Factor | >1.48 | >20.83 | 1.0 | 1.0 | 2.0 | >1.04 | 4.1 |
| Insecticide + Example 15 | 2.5 | 100 | 0.02 | 0.1 | >0.03 | 0.007 | .02 |
| Example 15 | >100 | 10,000 | >0.1 | >0.1 | .2 | >0.1 | .15 |
| Activating Factor | >1.2 | >16.67 | 1.0 | 1.0 | — | >12.0 | 3.75 |
| Insecticide + Example 16 | 3.0 | 100 | 0.02 | 0.05 | 0.02 | 0.02 | .07 |
| Example 16 | >100 | >10,000 | >0.1 | >0.1 | >.2 | >0.1 | >.2 |
| Activating Factor | >1.0 | >16.67 | 1.0 | >1.9 | >3.33 | >4.2 | >1.22 |
| Insecticide + |  |  |  |  |  |  |  |

TABLE II-continued

|  | Susceptable HF | Resistant HF | GR | SMC | CL | TBW | GPR |
|---|---|---|---|---|---|---|---|
| Example 17 | 2.0 | 50.0 | 0.007 | 0.03 | 0.02 | 0.05 | .002 |
| Example 17 Activating Factor | 85 / 1.4 | 3,000 / >11.32 | >0.1 / >2.4 | 0.1 / 3.2 | .15 / 3.0 | >0.1 / >1.67 | .07 / 23.9 |
| Insecticide + Example 18 | 1.8 | 30 | 0.007 | 0.02 | 0.02 | .007 | .003 |
| Example 18 Activating Factor | 80 / 1.6 | 800 / >5.2 | >0.1 / >2.4 | 0.1 / 4.7 | .08 / 2.22 | 0.1 / 12.0 | .07 / 15.9 |
| Insecticide + Example 19 | 2.0 | 70.0 | 0.02 | 0.05 | >0.03 | 0.05 | .003 |
| Example 19 Activating Factor | >100 / >1.5 | 3,000 / >8.1 | >0.1 / 1.0 | >0.1 / >1.9 | .03 / — | >0.1 / >1.67 | .08 / 17.4 |
| Insecticide + Example 20 | 2.0 | 50 | 0.007 | 0.1 | 0.02 | 0.008 | .003 |
| Example 20 Activating Factor | >100 / 1.5 | 7000 / >24.5 | >0.1 / >2.4 | >0.1 / >1.0 | >.2 / 3.33 | >0.1 / >10.4 | .15 / 25.0 |
| Insecticide + Example 21 | 2.0 | 80.0 | 0.02 | >.01 | 0.005 | >0.1 | .07 |
| Example 21 Activating Factor | >100 / >1.5 | >10,000 / >20.83 | >0.1 / 1.0 | >0.1 / 1.0 | .2 / 13.33 | >0.1 / — | .15 / 1.0 |
| Insecticide + Example 22 | 1.5 | 50.0 | 0.007 | 0.1 | 0.007 | 0.1 |  |
| Example 22 Activating Factor | >100 / >2.0 | 8,000 / 727.58 | >0.1 / >2.4 | >0.1 / >1.0 | >.2 / >9.5 | >0.1 / >1.0 |  |
| Insecticide + Example 23 | 2.0 | 300.0 | 0.007 | >0.1 | >0.03 | 0.007 | .003 |
| Example 23 Activating Factor | 100 / 1.5 | >10,000 / >5.55 | >0.1 / >2.4 | >0.1 / — | >.2 / — | >0.1 / >11.9 | .18 / 27.27 |
| Insecticide + Example 24 | 2.0 | 300.0 | 0.015 | >0.1 | — | 0.01 | .007 |
| Example 24 Activating Factor | >100 / >1.5 | >10,000 / >5.55 | >0.1 / 1.0 | >0.1 / — | >.2 / — | >0.1 / >8.3 | >.2 / >12.2 |
| Insecticide + Example 25 | 2.8 | >1,000 | — | 0.1 | 0.03 | 0.05 | .1 |
| Example 25 Activating Factor | >100 / 1.0 | >10,000 / — | >0.1 / — | 0.1 / — | >.2 / >2.2 | >0.1 / >1.67 | >.2 / 1.0 |

*Insecticide = N-(mercaptomethyl) phthalimide-S-(O,O-dimethylphosphorodithioate).

The compositions of this invention are generally embodied into a form suitable for convenient application. For example, the compositions can be embodied into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed as the sole pesticide component or they can be used in admixture with other compounds having similar utility. The pesticide formulations of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compositions can be applied directly to feedstuffs, seeds, etc., upon which the pests feed. Then applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the compound is ingested into the body of the pest.

The precise manner in which the pesticidal compositions of this invention are used in any particular instance will be readily apparent to a person skilled in the art. Generally, the active pesticide composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

The term "lower alkyl" is intended to include straight or branched chain alkyl groups having 1–6 carbon atoms. The term "alkyl" is intended to include straight or branched chain alkyl groups having 1–10 carbon atoms. The term "lower alkoxy" includes a radical having 1–6 carbon atoms and "cycloalkyl" includes a radical having 3–8 carbon atoms.

What is claimed is:

1. An insecticidally active composition comprising an insecticidally effective amount of an insecticide which is N-(mercaptomethyl) phthalimide-S-(O,O-dimethylphosphorodithioate) and an amount effective to enhance the activity thereof of an activator having the formula:

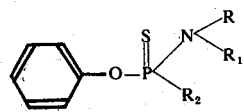

wherein R is selected from the group consisting of hydrogen and lower alkyl having from 1–6 carbon atoms; $R_1$ is selected from the group consisting of hydrogen, alkyl having from 1–10 carbon atoms and cyclohexyl and $R_2$ is selected from the group consisting of lower alkoxy having from 1–6 carbon atoms and $$-N\begin{matrix}R_3\\R_4\end{matrix}$$

wherein $R_3$ and $R_4$ are the same or different and are selected from the group consisting of hydrogen and lower alkyl having from 1–6 carbon atoms; said activator being present in an amount ranging between 0.1 and 10 parts by weight per part by weight insecticide.

2. The composition of claim 1 wherein R is —H, $R_1$ is —H and $R_2$ is —OCH$_3$.

3. The composition of claim 1, wherein R is —H, $R_1$ is $$-CH\begin{matrix}CH_3\\CH_3\end{matrix}$$

and $R_2$ is —OCH$_3$.

4. The composition of claim 1, wherein R is —H, $R_1$ is —(CH$_2$)$_9$—CH$_3$ and $R_2$ is —OCH$_3$.

5. The composition of claim 1, wherein R is —CH$_3$, $R_1$ is —CH$_3$ and $R_2$ is —OCH$_3$.

6. The composition of claim 1, wherein R is —H, $R_1$ is (thiophene ring with S)

and $R_2$ is —OCH$_3$.

7. The composition of claim 1, wherein R is —H, $R_1$ is —H and $R_2$ is —OC$_2$H$_5$.

8. The composition of claim 1, wherein R is —H, $R_1$ is —CH$_3$ and $R_2$ is —NHCH$_3$.

9. The composition of claim 1, wherein R is —C$_2$H$_5$, $R_1$ is —C$_2$H$_5$ and $R_2$ is $$-N\begin{matrix}C_2H_5\\C_2H_5\end{matrix}$$

10. The composition of claim 1, wherein R is —H, $R_1$ is —CH$_3$ and $R_2$ is —OCH$_3$.

11. The composition of claim 1, wherein R is —H, $R_1$ is $$-CH_2-CH\begin{matrix}CH_3\\CH_3\end{matrix}$$

and $R_2$ is —OCH$_3$.

12. The composition of claim 1, wherein R is —C$_2$H$_5$, $R_1$ is —C$_2$H$_5$ and $R_2$ is —OCH$_3$.

13. The composition of claim 1, wherein R is —H, $R_1$ is —(CH$_2$)$_2$—CH$_3$ and $R_2$ is —OCH$_3$.

14. The composition of claim 1, wherein R is —H, $R_1$ is $$-CH(CH_3)-CH_2-CH_3$$

and $R_2$ is —OCH$_3$.

15. The composition of claim 1, wherein R is —H, $R_1$ is —(CH$_2$)$_5$—CH$_3$ and $R_2$ is —OCH$_3$.

16. The composition of claim 1, wherein R is —H, $R_1$ is —(CH$_2$)$_7$—CH$_3$ and $R_2$ is —OCH$_3$.

17. The composition of claim 1, wherein R is —H, $R_1$ is —(CH$_2$)$_8$—CH$_3$ and $R_2$ is —OCH$_3$.

18. The composition of claim 1, wherein R is —H, $R_1$ is —CH$_3$ and $R_2$ is —OC$_2$H$_5$.

19. The composition of claim 1, wherein R is —H, $R_1$ is C$_2$H$_5$ and $R_2$ is —OC$_2$H$_5$.

20. The composition of claim 1, wherein R is —H, $R_1$ is C$_3$H$_7$ and $R_2$ is —OC$_2$H$_5$.

21. The composition of claim 1, wherein R is —H, $R_1$ is —(CH$_2$)$_3$—CH$_3$ and $R_2$ is —OC$_2$H$_5$.

22. The composition of claim 1, wherein R is —H, $R_1$ is —(CH$_2$)$_4$—CH$_3$ and $R_2$ is —OC$_2$H$_5$.

23. The composition of claim 1, wherein R is —H, $R_1$ is —H and $R_2$ is —O(CH$_2$)$_4$—CH$_3$.

24. The composition of claim 1, wherein R is —H, $R_1$ is —C$_2$H$_5$ and $R_2$ is —NH-C$_2$H$_5$.

25. The composition of claim 1, wherein R is —H, $R_1$ is —(CH$_2$)$_2$—CH$_3$ and $R_2$ is —NH(CH$_2$)$_2$—CH$_3$.

26. the composition of claim 1, wherein R is —H, $R_1$ is —(CH$_2$)$_3$—CH$_3$ and $R_2$ is —NH—(CH$_2$)$_3$—CH$_3$.

* * * * *